United States Patent
Batterson et al.

(10) Patent No.: US 11,364,137 B2
(45) Date of Patent: *Jun. 21, 2022

(54) ORTHOPEDIC WALKING BRACE HAVING A CURVED SOLE

(71) Applicant: DJO, LLC, Vista, CA (US)

(72) Inventors: Benjamin Batterson, San Marcos, CA (US); Manikandan Sasidharan, South Portland, ME (US); Christopher P. Loughnane, Nashua, NH (US); Derek Hugger, Goffstown, NH (US); Lee Panecki, Somerville, MA (US); Chris Aiston, Mont Vernon, NH (US)

(73) Assignee: DJO, LLC, Vista, CA (US)

(*) Notice: Subject to any disclaimer, the term of this patent is extended or adjusted under 35 U.S.C. 154(b) by 359 days.

This patent is subject to a terminal disclaimer.

(21) Appl. No.: 16/519,272

(22) Filed: Jul. 23, 2019

(65) Prior Publication Data
US 2019/0343669 A1    Nov. 14, 2019

Related U.S. Application Data

(63) Continuation of application No. 15/295,440, filed on Oct. 17, 2016, now Pat. No. 10,376,403, which is a
(Continued)

(51) Int. Cl.
*A61F 5/01* (2006.01)
*A43B 3/02* (2006.01)
(Continued)

(52) U.S. Cl.
CPC .............. *A61F 5/0111* (2013.01); *A43B 3/02* (2013.01); *A43B 13/04* (2013.01); *A43B 13/12* (2013.01); *A43B 13/145* (2013.01); *A61F 5/0195* (2013.01)

(58) Field of Classification Search
CPC ........ A61F 5/01; A61F 5/0102; A61F 5/0111; A61F 5/0127; A61F 5/011; A61F 5/0195;
(Continued)

(56) References Cited

U.S. PATENT DOCUMENTS 5,491,909 A    2/1996    Darby
8,313,451 B2    11/2012    Cox
(Continued)

FOREIGN PATENT DOCUMENTS

CN    1374074 A    10/2002
CN    2838565      11/2006
(Continued)

OTHER PUBLICATIONS

International Search Report and Written Opinion issued in related PCT case PCT/US2014/026642, dated Jun. 27, 2014.
(Continued)

*Primary Examiner* — Caitlin A Carreiro
(74) *Attorney, Agent, or Firm* — Veros Legal Solutions, LLP

(57) ABSTRACT

Described herein are systems and devices for providing an orthopedic walking brace having a housing and a sole with a curved distal surface. The housing is configured to encompass and immobilize a patient's ankle against flexion. The distal surface of the sole has a posterior region, a mid region, and an anterior region. The posterior region is configured to lie under a heel portion of the patient's foot and has a first anterior-posterior (AP) curvature that increases from a posterior side of the posterior region toward a middle portion of the posterior region and decreases from the middle portion of the posterior region toward the mid region. The mid region is configured to lie under a center portion of the patient's foot. The anterior region is configured to lie under
(Continued)

an anterior metatarsal and toe portion of the patient's foot and has a second AP curvature.

18 Claims, 11 Drawing Sheets

Related U.S. Application Data continuation of application No. 14/211,097, filed on Mar. 14, 2014, now Pat. No. 9,468,551.

(60) Provisional application No. 61/792,129, filed on Mar. 15, 2013.

(51) Int. Cl.
*A43B 13/04* (2006.01)
*A43B 13/12* (2006.01)
*A43B 13/14* (2006.01)

(58) Field of Classification Search
CPC . A61F 5/0113; A61F 5/14; A43B 3/00; A43B 3/02; A43B 3/0036; A43B 13/00; A43B 13/02; A43B 13/14; A43B 13/141; A43B 13/04; A43B 13/12; A43B 13/145; A43B 13/146; A43B 5/00; A43B 5/0405; A43B 7/00; A43B 7/14; A43B 7/1405; A43B 7/141; A43B 7/1415; A43B 7/16; A43B 7/22; A43B 7/28
USPC .... 602/5, 23, 27, 28, 29; 36/1.5, 83, 84, 87, 36/88, 91, 92, 93, 3 B, 12, 25 R, 43, 44, 36/140, 145; 128/882, 892, 893
See application file for complete search history.

(56) References Cited

U.S. PATENT DOCUMENTS

| | | |
|---|---|---|
| 9,468,551 B2* | 10/2016 | Batterson .............. A43B 13/145 |
| 10,376,403 B2* | 8/2019 | Batterson .............. A61F 5/0111 |
| 2005/0171461 A1 | 8/2005 | Pick |
| 2007/0293798 A1 | 12/2007 | Hu et al. |
| 2009/0306565 A1 | 12/2009 | Chan |
| 2010/0069807 A1 | 3/2010 | Cox |
| 2010/0186255 A1 | 7/2010 | Avar et al. |
| 2012/0209163 A1 | 8/2012 | Phillips |

FOREIGN PATENT DOCUMENTS

| | | |
|---|---|---|
| CN | 101827568 A | 9/2010 |
| CN | 101842063 A | 9/2010 |
| CN | 101965168 A | 2/2011 |
| JP | 2007519497 A | 7/2007 |

OTHER PUBLICATIONS

Microfilm of JP Utility Model Application No. S47-90682 (JP S49-48795 U).

* cited by examiner

ORTHOPEDIC WALKING BRACE HAVING A CURVED SOLE

CROSS-REFERENCE TO RELATED APPLICATIONS

This application is a continuation of U.S. application Ser. No. 15/295,440 filed Oct. 17, 2016; which claims priority to U.S. application Ser. No. 14/211,097 filed Mar. 14, 2014; which claims priority to U.S. Provisional Patent Application No. 61/792,129, filed on Mar. 15, 2013. Each of these applications are hereby incorporated by reference herein in their entireties.

BACKGROUND

Field of the Disclosure

Orthopedic ankle casts and braces are designed to restrict ankle movement during recovery from injuries such as torn ligaments, sprained ankles, tibial stressed fractures and ankle fractures. An ankle cast is typically molded from rigid materials such as plaster or fiberglass. It supports the lower limb, holds the foot in a neutral position, and immobilizes the ankle. Casts are often worn for several weeks or months, preferably without any weight on the joint to allow proper healing of broken bones and torn ligaments.

During further rehabilitation and strengthening of the ankle after initial stabilization of the injury, walking braces are used instead of casts to continue immobilization of the ankle while allowing gradual increase in weight-bearing exercises such as walking. Some walking braces have a flat sole that is useful for standing, but difficult for walking. Some walking braces have a rocker sole to create a rolling-forward motion during stride, partially replacing lost functions of the ankle joint. Nonetheless, other joints in the hip and the knee often need to compensate for lost ankle movements, making the use of walking braces fatiguing. In addition, walking braces are large and heavy, with stiff brace housings, and large soles to accommodate the size of the housing. Some walking braces with a rocking bottom have a thick sole, which can cause hip displacement when the thickness is not matched on the patient's other foot. The added weight and height make it difficult to use a walking brace, and the resulting unnatural gait can lead to further knee or hip discomfort.

Thus, there is a need for a walking brace that will allow the patient to approximate a natural gait.

SUMMARY

Disclosed herein are systems and devices for providing walking braces having a sole with a curved distal surface. The sole thus provided has a distal surface with changing Anterior-Posterior (AP) curvatures and changing Medial-Lateral (ML) curvatures to enable a natural gait when walking and to enhance stability when the patient is in a standing position. Such curvature changes across the distal surface enable large AP curvatures without large increases in the overall thickness of the sole.

According to one aspect, a sole is configured for use with an orthopedic walking brace. The sole includes a proximal surface and a distal surface. The proximal surface is configured to receive a patient's foot, and the distal surface has a posterior region, a mid region, and an anterior region. The posterior region is configured to lie under a heel portion of the patient's foot and has a first anterior-posterior (AP) curvature that increases from a posterior side of the posterior region toward a middle portion of the posterior region and decreases from the middle portion of the posterior region toward the mid region. The mid region is configured to lie under a center portion of the patient's foot. The anterior region is configured to lie under an anterior metatarsal and toe portion of the patient's foot and has a second AP curvature.

In some embodiments, the anterior region comprises greater than or equal to 30% of an AP length of the distal surface and less than or equal to 40% of the AP length of the distal surface. In some embodiments, the mid region comprises greater than or equal to 35% of an AP length of the distal surface and less than or equal to 45% of the AP length of the distal surface. In some embodiments, the mid region is configured to lie directly beneath the midfoot. In some embodiments, the first AP curvature has a maximum value greater than about 0.25 $inch^{-1}$. In some embodiments, a product of an AP length of the posterior region and a maximum value of the first AP curvature has a maximum value less than about 0.7. In some embodiments, the second AP curvature has a maximum value greater than about 0.1 $inch^{-1}$. In some embodiments, a product of an AP length of the anterior region and a maximum value of the second AP curvature is greater than about 0.35. In some embodiments, the mid region is substantially flat. In some embodiments, the second AP curvature increases from a posterior side of the anterior region toward a middle portion of the anterior region and decreases from the middle portion of the anterior region toward an anterior side of the anterior region. In some embodiments, the distal surface has a first medial-lateral (ML) curvature that has a first peak adjacent to a medial edge, a second peak adjacent to a lateral edge of the distal surface and is substantially flat in between the first and the second peaks. In some embodiments, the distal surface is symmetric. In some embodiments, the proximal surface is rigid, and the distal surface is flexible. In some embodiments, the distal surface comprises a first material having a first density and a second material having a second density that is smaller than the first density. In some embodiments, the first material is rubber. In some embodiments, the second material is ethyl vinyl acetate. In some embodiments, the proximal surface is formed of a plastic material. In some embodiments, a distance between a highest point on the distal surface and a ground surface defines a thickness and a maximum value of the thickness is about 0.75 inches.

According to another aspect, a method of immobilizing an ankle against flexion while approximating a natural gait is provided. The method includes providing an orthopedic walking brace. The walking brace includes a housing configured to encompass a patient's ankle. The walking brace includes a curved sole having a proximal surface and a distal surface, the proximal surface configured to receive the patient's foot, and the distal surface having a posterior region, a mid region, and an anterior region. The posterior region is configured to lie under a heel portion of the patient's foot and has a first anterior-posterior (AP) curvature that increases from a posterior side of the posterior region toward a middle portion of the posterior region and decreases from the middle portion of the posterior region toward the mid region. The mid region is configured to lie under a center portion of the patient's foot. The anterior region is configured to lie under an anterior metatarsal and toe portion of the patient's foot and has a second AP curvature. The method includes encompassing the ankle of the patient in the housing. The curved sole is configured to provide a substantially smooth transition from heel-strike to mid-stance and from mid-stance to toe-off. In some embodiments, the curved sole provides a rolling motion at an angular velocity that mimics a natural walking gait cycle.

BRIEF DESCRIPTION OF THE DRAWINGS

The foregoing and other objects and advantages will be appreciated more fully from the following description, with reference to the accompanying drawings. These depicted embodiments are to be understood as illustrative and not as limiting in any way.

DETAILED DESCRIPTION OF CERTAIN INVENTIVE EMBODIMENTS

To provide an overall understanding of the systems and devices described herein, certain illustrative embodiments will now be described. For the purpose of clarity and illustration, these systems and devices will be described with respect to an orthopedic walking brace applied to a patient's lower leg and ankle. It will be understood by one of ordinary skill in the art that the systems and devices described herein may be adapted and modified as appropriate. These systems and devices may be employed in other suitable applications, such as for other types of braces that include a curved sole, and other such additions and modifications will not depart from the scope hereof.

Figure 1:
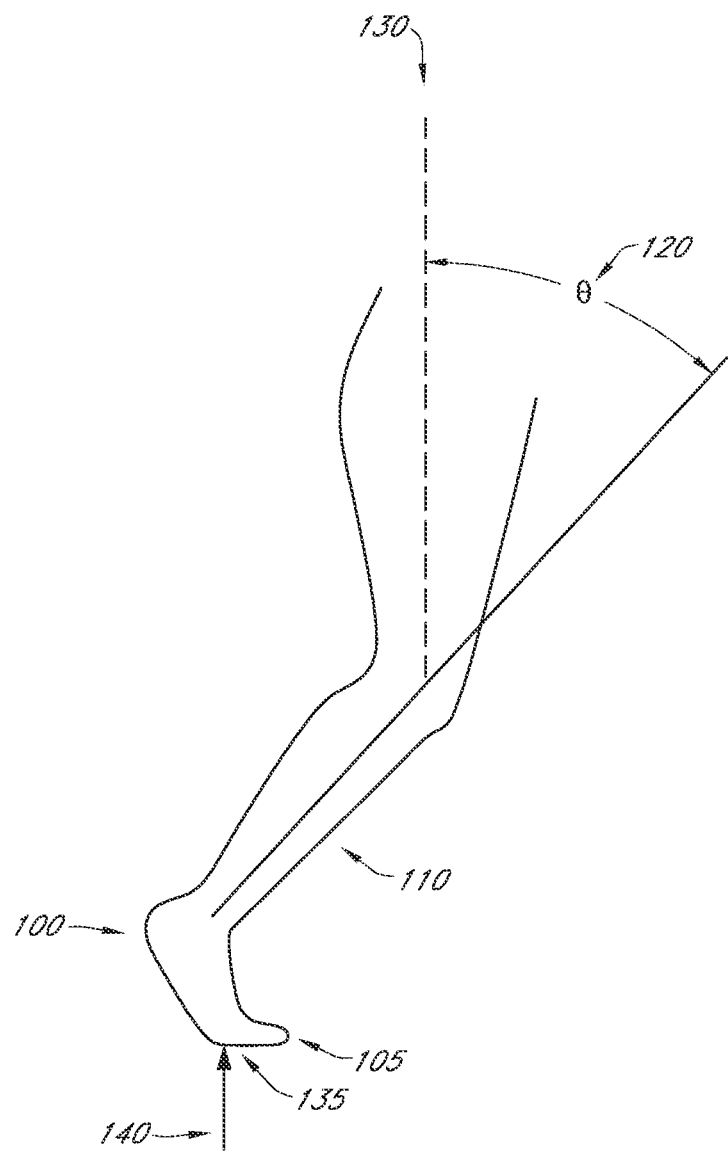
FIG. 1 is a diagram showing the shank angle.
Figure 2:
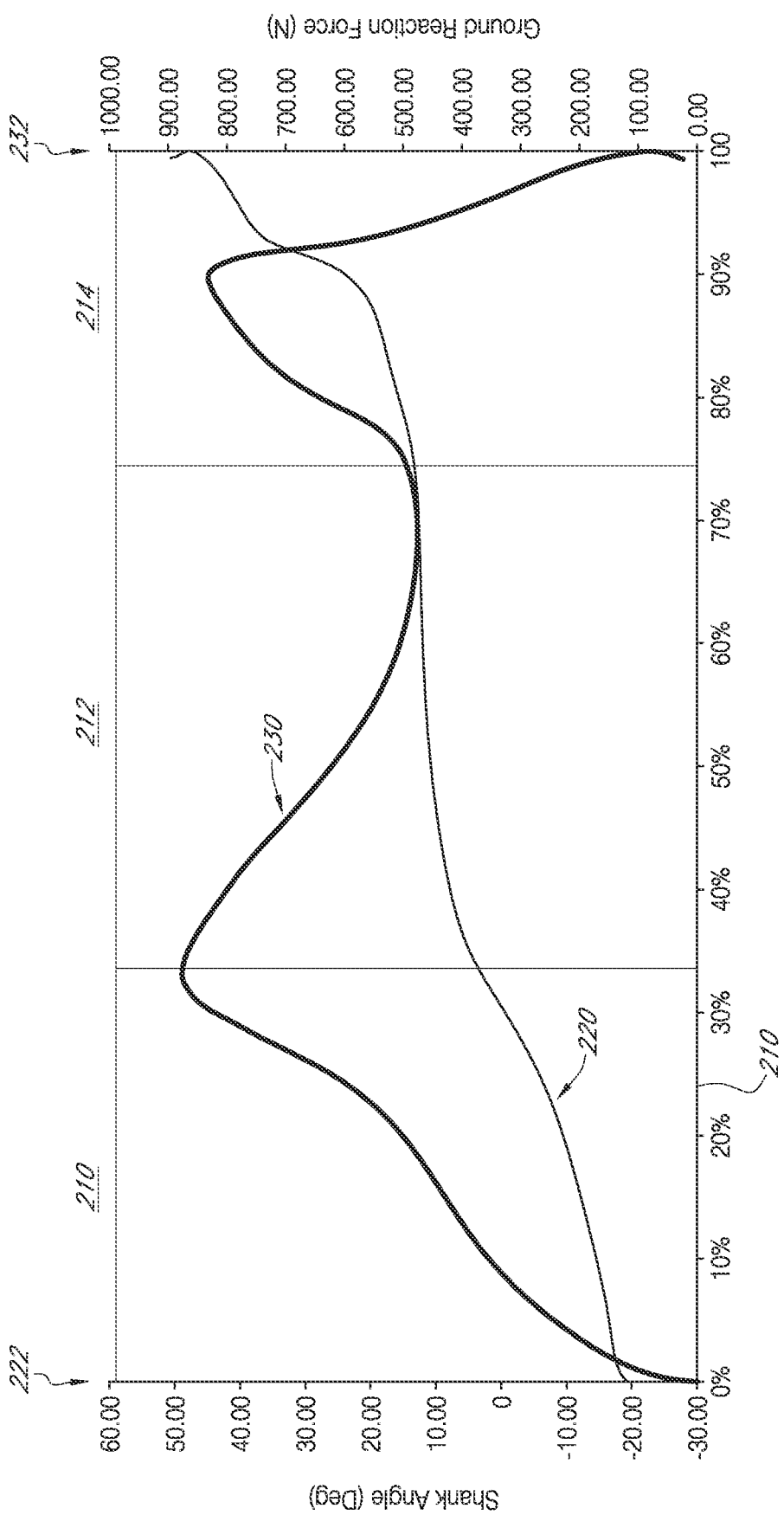
FIG. 2 is a plot showing illustrative measurements of shank angle and ground reaction force when walking.

FIG. 1 shows the shank angle 120 and FIG. 2 provides a corresponding curved line graph 220 of the shank angle 120 during the stance phase of the gait cycle. In FIG. 1, the lower limb of a person in a walking position is illustrated, with the anterior metatarsal and toe portion of the foot in contact with the ground. The shank angle 120 is measured clockwise from the vertical axis 130 when at least a portion of the distal surface of the foot is in contact with the ground. The shank angle 120 attains a value of 0 degrees if the shank and the thigh are aligned, as in an upright standing position; the shank angle 120 attains a positive value when the knee is flexed to the back as shown in FIG. 1 and attains a negative value when the lower leg is extended to the front beyond the upper thigh.

A gait cycle begins when a foot strikes the ground, and ends when the same foot strikes the ground again. The motion of a lower limb in a normal walking gait cycle can be divided into two phases, a stance phase during which the foot is in contact with and supported by the ground, and a swing phase during which the lower limb is swung forward by the hip and knee. The stance phase begins when the heel of the foot 100 strikes the ground, and ends when the toe 105 of the same foot leaves the ground. The stance phase can be further divided into three stages: heel-strike, mid-stance, and toe-off. As the name implies, heel-strike occurs when the heel strikes the ground and rolls forward. Mid-stance occurs when the foot is flat on the ground, with the body center of gravity directly above the foot. Toe-off follows mid-stance, and occurs when the anterior metatarsal, or the ball of the foot, and the toes push off the ground to propel the body forward. During the stance phase, the ankle and midtarsal joints provides dorsiflexion and plantar flexion movements, while the anterior metatarsal and toe portion of the foot provides forward propulsion.

The shank angle 120, and the foot center of pressure 135 continuously change throughout the stance phase, with larger changes in the shank angle 120 during heel-strike and toe-off, as indicated by the curved line graph 220 in FIG. 2. The horizontal axis 210 of this graph corresponds to the time span of the stance phase in percentages, or the percentage of the stance phase that has been completed. The primary vertical axis 222 represents the shank angle 120 in degrees. Shadings are used in FIG. 2 to approximate the three stages of the stance phase: regions 210, 212, and 214 correspond to heel-strike, mid-stance, and toe-off, respectively. Although measurements of shank angles for different individuals are expected to follow the same general pattern as the line graph 220 through the stance phase, individual variations and step-wise variations exist. The curved line graph 220 is presented as an illustrative example. Similar graphs can be drawn on an individual or other basis. As a person walks, the shank angle changes in a fashion similar to the curved line graph 220. Together, the ankle, tarsal, and metatarsal joints support such movements with a rolling motion of the foot while the foot is in contact with the ground. For a patient wearing an orthopedic walking brace, however, ankle movements are restricted. As a result, either the patient takes smaller steps, or the knee and hip joints compensate with additional flexion and extension. Both situations result in an unnatural gait that deviates significantly from the curved line graph 220. Knee and hip discomforts also occur after prolonged periods of use.

Figure 3:
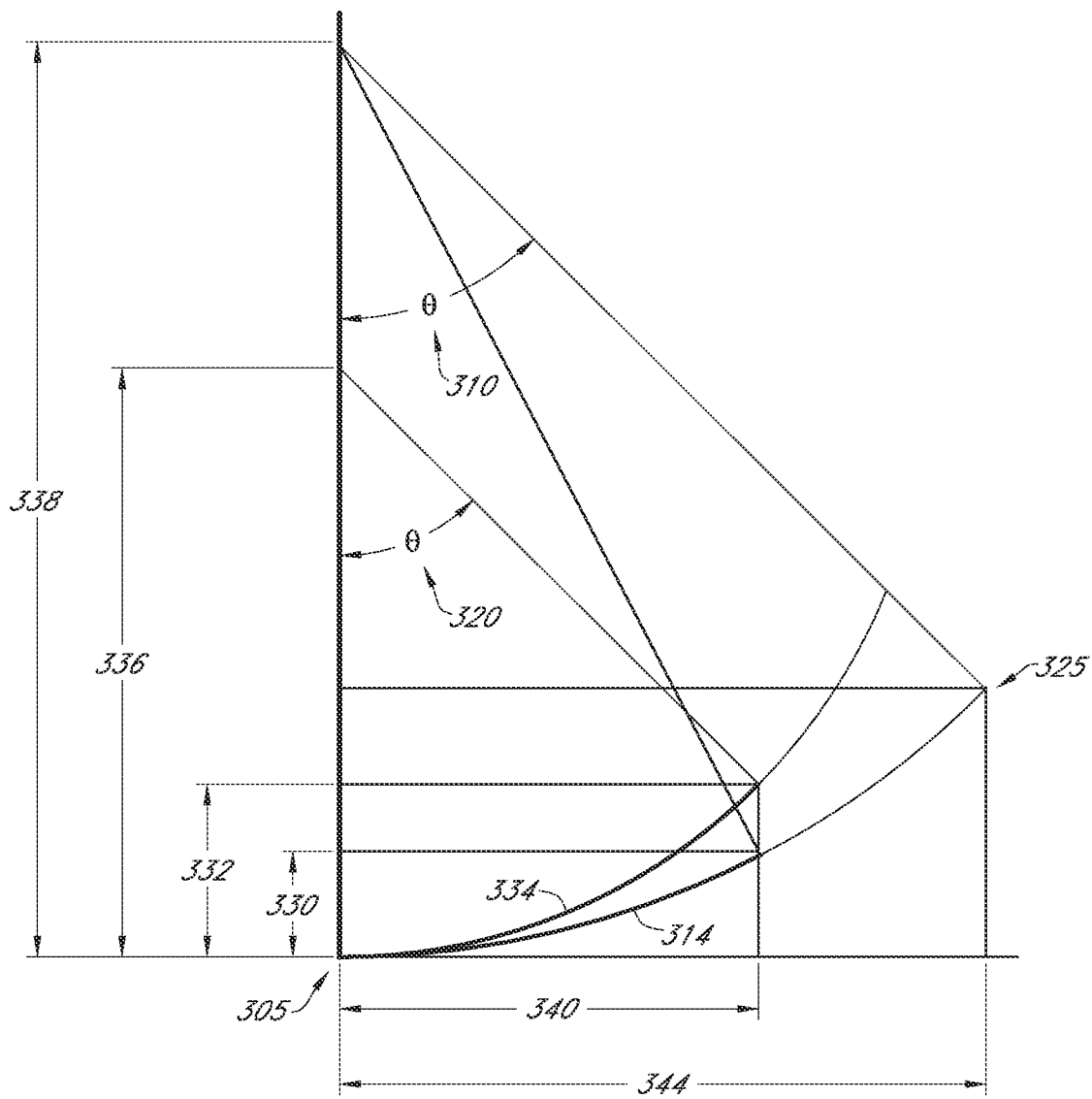
FIG. 3 illustrates the relationship between shank angle, curvature, and sole thickness.

To help patients wearing a walking brace achieve a rolling motion of the foot to better approximate a natural gait, soles for walking braces are often designed to have a rocker bottom, or curved distal surface, to facilitate changes in the shank angle as it would during natural gait. FIG. 3 illustrates the relationship between the shank angle and the AP curvature of the sole in an abstract fashion. Circular arcs 334 and 314 correspond to the same Anterior-Posterior (AP) length 340 but different curvatures, where curvature is defined as the reciprocal of the corresponding radii 336 and 338. In the case of non-circular arcs, curvatures change from point to point on the arc. The arcs 334 and 314 represent side views of the anterior portions of curved soles, with the point 305 corresponding to where the anterior portion joins a substantially flat mid portion. It is easy to see from FIG. 3 that a small curvature (e.g., a large radius 338) in the AP direction provides a flatter sole, while a large AP curvature (e.g., a small radius 336) supports a larger change in shank angle and propels the user forward. Angles 310 and 320 in FIG. 3 represent the amount of change in shank angle required to approximate toe-off during natural gait. These two angles are of the same value. The angle 320 corresponds to the arc 334.

Analogous to the arc 314, in many walking braces, the AP curvature at the anterior end is too small to provide sufficient change in shank angle, causing the patient to take smaller and uneven steps. Analogous to the arc 334 where the corresponding height 332 is larger than the height 330 of the arc 314, in many walking braces that do provide a more ideal curvature in the anterior portion or throughout the distal surface of the sole, the sole is substantially thicker, since the foot needs to lie on a flat surface when standing. A thicker sole leads to uneven leg lengths and hip displacement if this thickness is not matched on the patient's other foot. In yet some other walking braces where thickness is controlled with smaller curvature but a given change in shank angle is still desired, the anterior portion of the sole has a longer AP length, analogous to extending the arc 314 towards the point 325 to approach the angle 310. The AP length 344 of the arc between the point 305 and the point 325, with the larger radius 338 and corresponding to the angle 310, is much larger than the AP length 340 corresponding to arcs 334 and 314. A longer anterior portion pushes the mid portion of the sole towards the back, possibly affecting stability when a patient is in a standing position.

Figure 4:
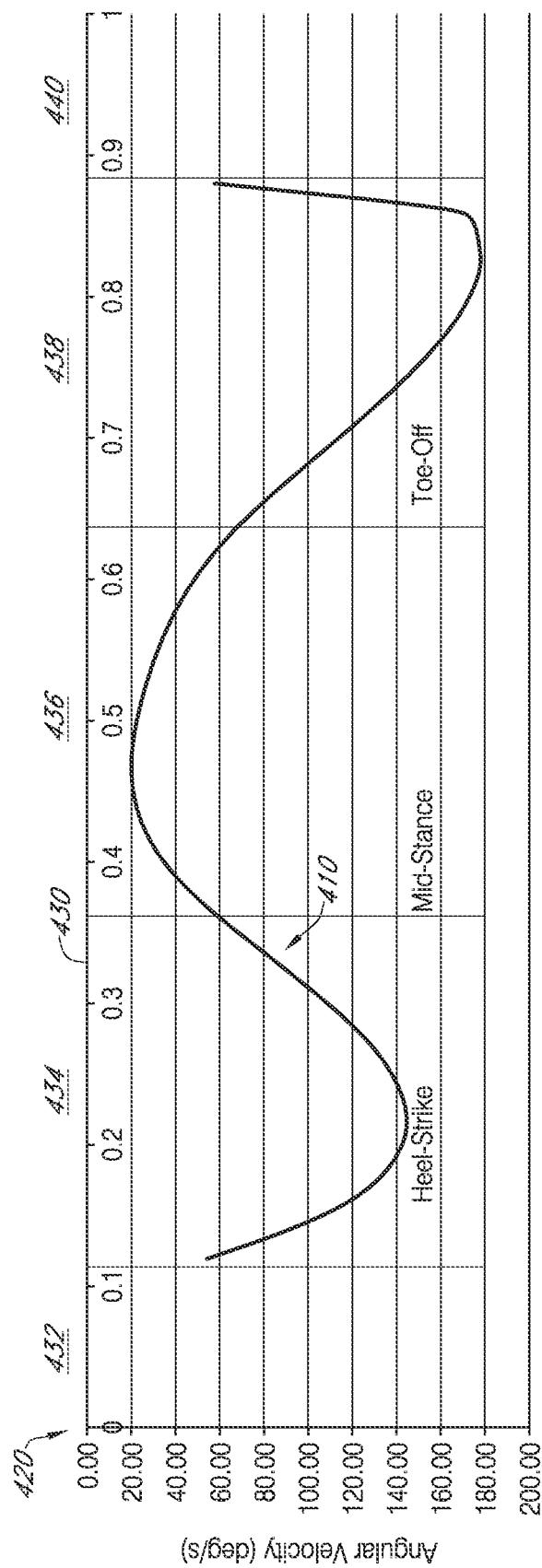
FIG. 4 is a plot showing illustrative shank angular velocity during a normal walking gait cycle.

Unlike previous walking braces, in one aspect of the systems and devices described herein, the distal surface of the sole is designed according to the rate at which the shank angle changes throughout the stance phase. In other words, in addition to achieving a particular change in shank angle, some embodiments allow rolling motion of the walking brace to occur at an angular velocity that mimics a natural walking gait cycle, as shown in FIG. 4. These embodiments are advantageous over previous curved soles for walking braces because these embodiments provide sufficient acceleration in the anterior and posterior portions of the sole to propel the user forward without incurring excessive thickness. These embodiments also allow the mid portion of the sole to span over a longer length, and to lie beneath the center portion of the foot for improved stability. In addition, with such designs where the distal surface curves according to the rate at which the shank angle changes throughout the stance phase, the mid portion of the sole has a small but nonzero curvature, so that transitions from heel-strike to mid-stance and from mid-stance to toe-off are both gradual and smooth. Such small curvatures in the mid-portion of the sole do not cause stability problems when a user is standing, in part because a combination of semi-rigid and flexible materials causes the weight-bearing mid portion to become essentially flat when the body mass stays directly on top.

FIG. 4 provides a curved line graph 410 of typical shank angular velocity during a normal walking gait cycle. The horizontal axis 430 represents the span of the gait cycle using percentages, with regions 434, 436 and 438 approximate the heel-strike, mid-stance, and toe-off stages of the stance phase, respectively. Regions 432 and 440 correspond to the swing phase during which changes in shank angle are facilitated by hip and knee joints directly. The vertical axis 420 extends downward and shows that the shank angular velocity varies between about 20 deg/s and about 180 deg/s. The curved line graph 410 shown in FIG. 4 is obtained by averaging angular velocity measurements from a plurality of individuals. In some embodiments of the walking brace where the sole is customized individually or customized for a particular group of patients, the desired angular velocity graph may differ from the curved line plot 410, while still retaining a similar shape, with one valley in the heel-strike stage, one hill in the mid-stance stage, and one valley in the toe-off stage.

Returning to FIG. 2, also shown is a curved line graph 230 on the secondary vertical axis 232, representing the ground reaction force 140 (see FIG. 1), which is the force exerted by the ground on the foot during the stance phase of the gait cycle, when body weight passes over the foot as the shank and the rest of body move forward. The horizontal axis 210 represents the percentage of the stance phase that has been completed. At the beginning of heel-strike (approximately 0%) and the end of toe-off (approximately 100%), the reaction force is about 0 Newton (N). Since in general, the amount of force going through the foot is dependent on the patient's body weight, the curved line graph 230 is presented as an illustrative example only. During heel-strike and toe-off, the foot serves as a rigid lever to propel the body forward, causing the force 140 to be much larger than the patient's body weight. During mid-stance, the other foot is off the ground, and the patient's center of gravity is directly over the foot in the walking brace. Thus, the mid portion of the sole, corresponding to mid-stance, should be substantially flat in the AP direction to provide stability, whether the patient is walking or standing. In some embodiments, the mid portion of the sole is substantially flat, and configured to lie under a center portion of the patient's foot, without comprising maximum curvature achievable in the anterior or posterior end. In some embodiments, the mid portion of the sole is configured to lie directly beneath the midfoot.

Furthermore, although not shown explicitly in a figure here, normally the foot center of pressure flows through the foot continuously starting from the slightly lateral side of the heel towards the front in a medial direction, exiting between the first and the second metatarsal and through the big toe. For walking braces with soles flat in the Medial-Lateral (ML) direction, any slight inversion or eversion of the lower leg results in the foot center of pressure jumping out to the edge of the sole, a discrete event that interrupts a smooth gait. In one aspect of the systems and devices described herein, the ML curvature is large enough to accommodate a normal gait, and also small enough to allow stable standing. Such a feature is approximated by having, at each ML cross-section, an ML curvature that has a peak adjacent to the medial edge and another peak adjacent to the lateral edge of the distal surface, while being substantially flat in between the two peaks. To further mimic the progression of the foot center of pressure, ML curvatures vary gradually from the posterior of the sole to the anterior, with larger peak values near the heel and smaller peak values at the mid portion.

Figure 5:
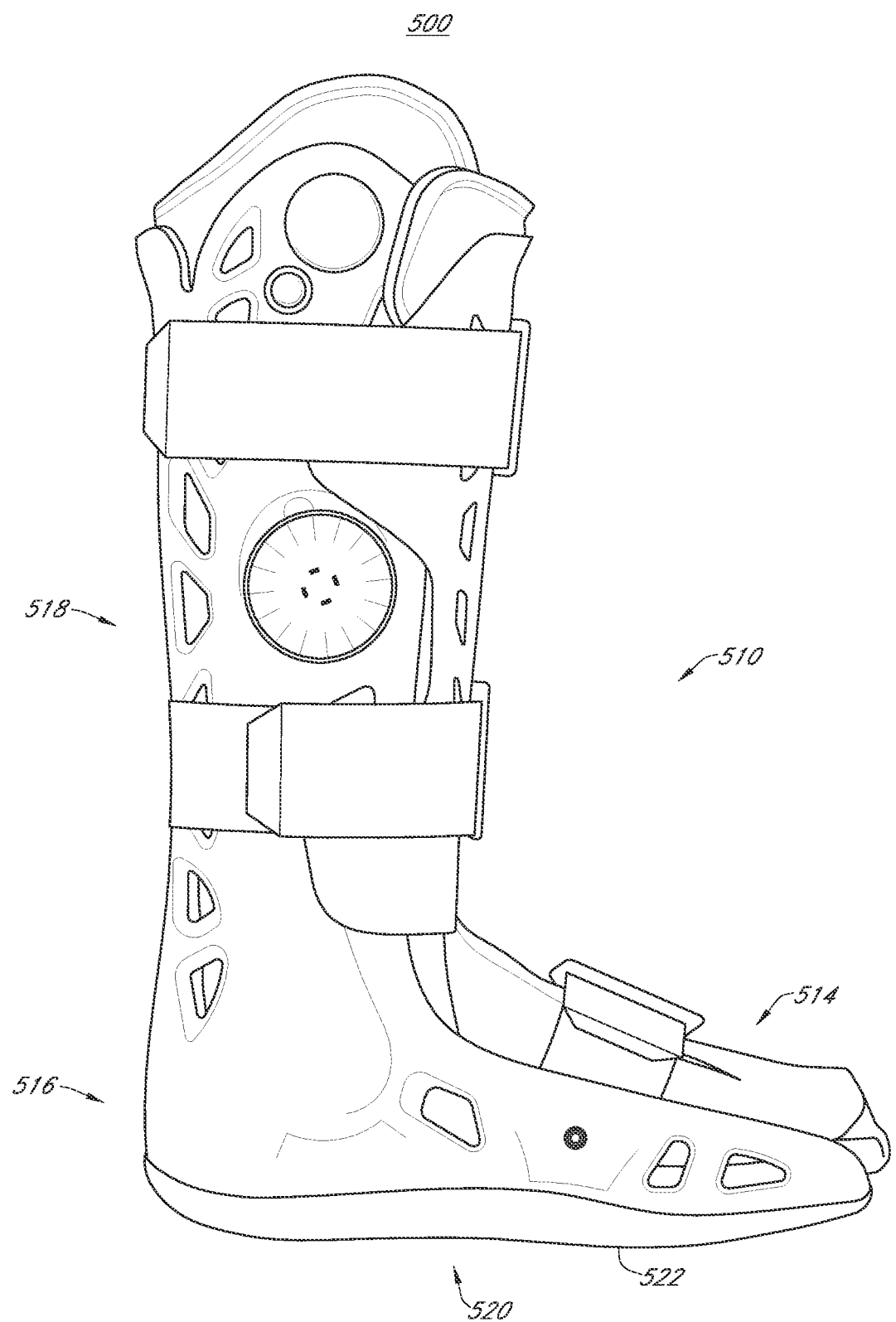
FIG. 5 is a side view of an illustrative walking brace having a curved sole, in accordance with one embodiment.

FIG. 5 shows an embodiment of an orthopedic walking brace 500 with a brace housing 510 and a sole 520, which has a curved distal surface 522. The brace housing 510 can have any suitable form for providing support to the lower leg and the foot. In this embodiment, the brace housing 510 is a rigid shell that has a footbed portion 514, a heel portion 516, and an upright support portion 518. The footbed portion 514 has a planar surface on the bottom for direct attachment to the sole 520, and may enclose the patient's foot entirely or partially. The inside of the housing 510 may be lined with cushioning material such as foam pads and inflatable components to provide comfort and to allow the user to adjust compression level provided by the housing. In some embodiments, instead of a rigid shell that immobilizes the ankle entirely, the housing can be made of a semi-rigid material to allow small ankle movements during the recovery process.

Figure 6:
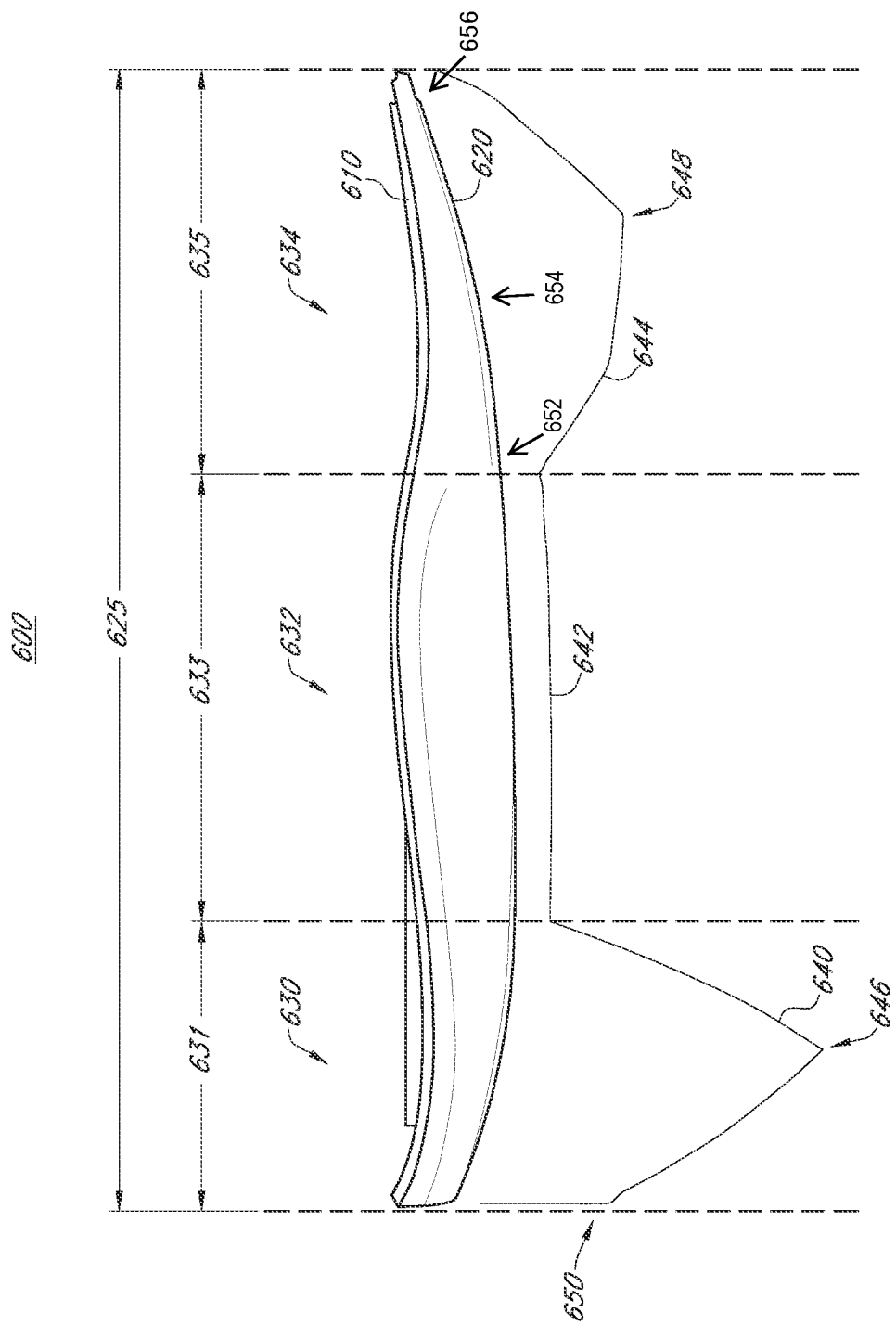
FIG. 6 is a side view of an illustrative curved sole, in accordance with one embodiment, with a curvature plot for its distal surface.

FIG. 6 shows an illustrative embodiment 600 of a curve sole, with proximal surface 610 and distal surface 620. The distal surface 620 has a curvature that approximates the angular velocity graph 410 plotted in FIG. 4. Starting from the most posterior point, the sole 600 can be divided into three regions: a posterior region 630, a mid region 632, and an anterior region 634. The posterior region 630 extends from the most posterior point of the sole 600 to the mid region 632. The mid region 632 extends from the posterior region 630 to the anterior region 634. The anterior region 634 extends from the mid region 632 to the most anterior point of the sole 600. The AP length 625 of the sole 600 is dependent on the size of the orthopedic walking brace. For example, a medium-sized men's walking brace may have an AP length 625 of about 11 inches. Walking braces designed for children are made proportionately smaller. The mid region 632 provides stability support to the patient when standing. The AP length 633 of the mid region 632 may be within the range of about 35% to about 45% of the AP length 625 of the sole 600, and in one example, is about 40% of the AP length 625 of the sole 600. The AP length 635 of the anterior region 634 may be within the range of about 30% to about 40% of the AP length 625 of the sole 600, and in one example, is about 35% of the AP length 625 of the sole 600. The length 631 of the posterior region 630 can be derived if both the AP length 633 of the mid region 632 and the AP length 635 of the anterior region 634 are known. According to various examples, the AP length 631 of the posterior region 630 is within the range between about 15% to about 35% of the AP length 625 of the sole 600. In some embodiments, the AP length 631 of the posterior region 630 is about 25% of the AP length 625 of the sole 600. The posterior region 630, the mid region 632, and the anterior region 632 correspond to the heel-strike, mid-stance, and toe-off stages of the stance phase of the gait cycle, respectively.

As shown in FIG. 6, in some implementations, the toe-off anterior region 634 has an AP curvature 644 that increases from a posterior side to reach a maximum value 648, then decreases towards the anterior side. The maximum value 648 lies approximately within the middle portion of the anterior region 634. In some implementations, the maximum AP curvature 648 is greater than about 0.10 inch$^{-1}$. For example, it may be about 0.11 inch$^{-1}$.

When the size of a walking brace changes, the size of the sole changes as well. Shank angular velocity measurements for patients requiring walking braces of different sizes may or may not differ from the curved line graph 410 shown in FIG. 4, in part or entirely. Accordingly, when the AP length 625 of the sole 600 in FIG. 6 changes, the AP curvature of the distal surface 620 may be a scaled version of the AP curvatures 644, 642, and 640 for the embodiment shown in FIG. 6. For example, the AP curvature 644 of the anterior region 634 may retain the same shape, range of values, and maximum value 648, when the AP length 635 of the anterior region 634 changes in proportion to the AP length 625 of the sole 600. Similar rules may apply to the curvature 642 of the mid region 632 and the curvature 640 of the posterior region 630.

In some implementations, when the AP length 635 of the anterior region 634 changes in proportion to the AP length 625 of the sole 600, the AP curvature 644 of the anterior region 634 also changes according to a desired scaled factor. For example, in FIG. 3, the ratio between the AP length 340 and the radius 336 is the sine function of the angle 320. Therefore, this ratio remains constant when the AP length 340 and the radius 336 change in value, as long as the angle 320 stays constant. Similarly, in some implementations of the sole 600 shown on FIG. 6, the ratio between the AP length 635 of the anterior region 634 and the radius corresponding to the maximum curvature 648 of the anterior region 634 stays approximately the same when the sole 600 changes in size. In some implementations, the product of the maximum AP curvature 648 of the anterior region 634 and the AP length 635 of the anterior region 634 is greater than about 0.35.

In some other implementations, the net forward velocity of the patient's body is assumed to follow approximately the same pattern and range of values throughout the gait cycle among all people. The net forward velocity is also the tangential velocity at the sole, and the tangential velocity at the sole is the product of shank angular velocity and the radius of the curvature measured at the tangential point. Accordingly, when the sole 600 changes in size, the ratio of measured shank angular velocities and corresponding curvature of the sole retains approximately the same pattern and range of values.

In some embodiments, the heel-strike posterior region 630 has an AP curvature 640 that increases from a posterior side of the posterior region 630 to reach a maximum value 646, then decreases towards the mid region 642. The maximum value 646 lies approximately within the middle portion of the posterior region 630. In some implementations, the AP curvature 640 of the posterior region 630 attains a value 650 much larger than zero at the most posterior point of the sole 600. The maximum AP curvature 646 may be less than about 0.25 inch$^{-1}$. In one example, it is about 0.21 inch$^{-1}$. According to one implementation, the product of the maximum AP curvature 646 of the posterior region 630 and the AP length 631 of the posterior region 630 is less than about 0.7.

As discussed above with respect to FIG. 2, the mid region 632 of the sole 600 is configured to lie under a center portion of the patient's foot, and may lie directly beneath the midfoot. Additionally, the mid region 632 is substantially flat. Thus, the mid region 632 has an AP curvature 642 that stays approximately constant over the region. According to one example, the mid region 632 has an AP curvature 642 between about 0.024 inch$^{-1}$ and about 0.026 inch$^{-1}$. In some embodiments, the AP curvature 642 of the mid region 632 has a maximum value less than about 0.030 inch$^{-1}$. According to one implementation, the product of the maximum value of the AP curvature 642 of the mid region 632 and the AP length 633 of the mid region 632 is less than about 0.15.

Figure 7:
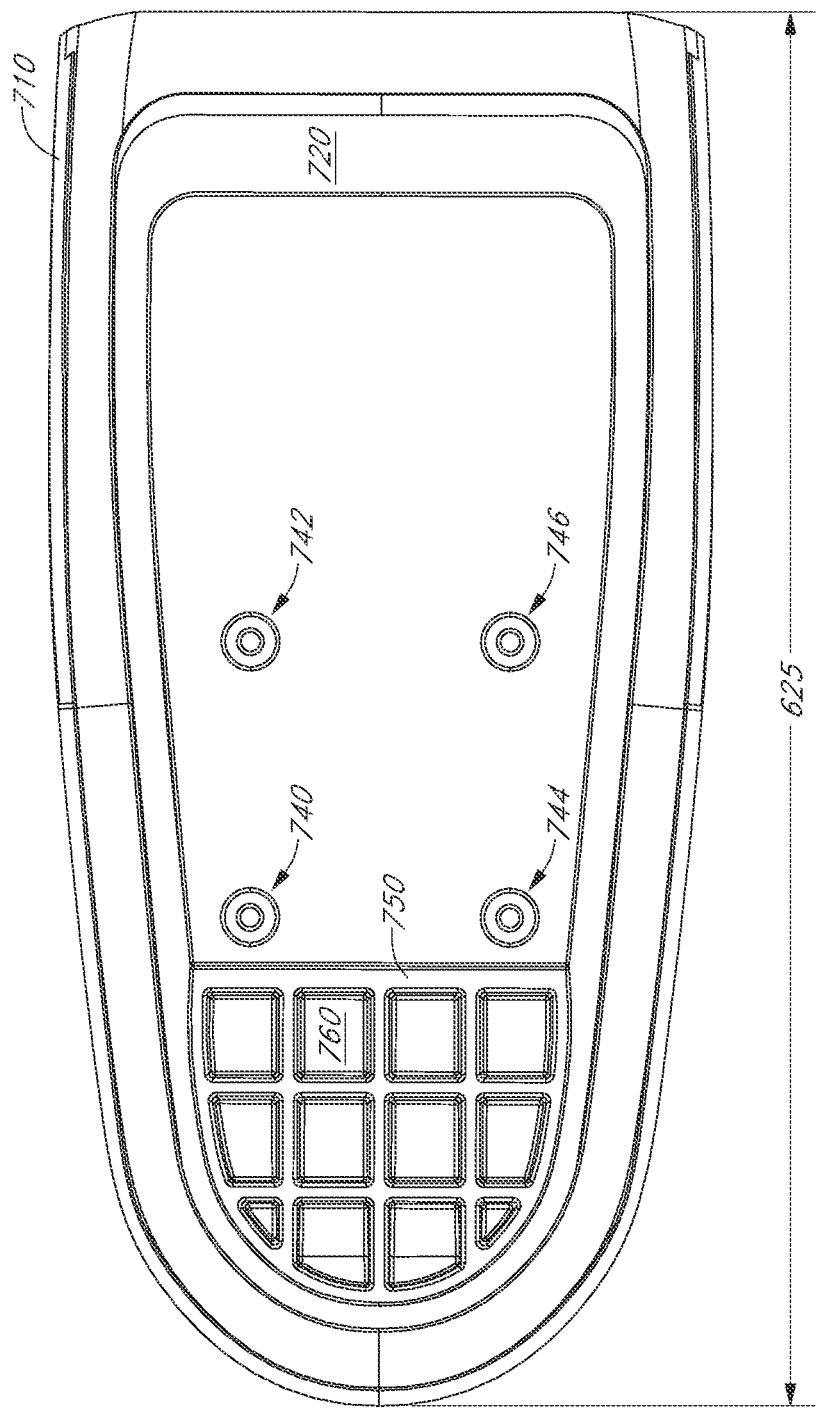
FIG. 7 is a projection of the proximal surface of the illustrative curved sole in FIG. 6, in accordance with one embodiment.

FIG. 7 shows the projection of the proximal surface 610 of the curved sole 600 in FIG. 6, according to one embodiment. The proximal surface 610 is configured to receive the patient's foot and the footbed 514 (see FIG. 5). According to various implementations, the sole 600 can be attached to the footbed 514 by adhesive, by interlocking mechanisms that allow the sole 600 to be removed and changed if necessary, or by both an adhesive and an interlocking mechanism. As shown in the illustrative embodiment in FIG. 7, the proximal surface 610 includes a circumferential rim 710, a circumferential groove 720, a raised platform 750 with recessed volumes 760, positioned under the heel, and circular notches 740, 742, 744, and 746. The circumferential rim 710, the circumferential groove 720, the raised platform 750, and the circular notches 740, 742, 744 and 746, on the proximal surface 610, can be coupled to corresponding structures (not shown) on the bottom of the footbed 514 to allow precise and secure attachment of the sole 600 to the footbed 514, which is part of the upper housing 510. The upper housing 510 supports the ankle and the lower leg. The AP length 625 of the sole 600 is dependent on the size of the upper housing 510. In other embodiments, the proximal surface 610 includes different structures for securing the sole 600 to the footbed 514. For example, the proximal surface 610 may include protrusions that couple with indents in the footbed 514.

In FIG. 7, the proximal surface 610 is symmetrical around the longitudinal axis. In one implementation, the distal surface 620 of the sole 600 shown in FIG. 6 is also symmetrical, allowing the sole 600 to be used for either a left or a right foot. In other implementations, the proximal surface 610 is designed with asymmetric structures. For example, instead of having a notch 742 as a mirror image of the notch 746, and a notch 740 as a mirror image of the notch 744, in some embodiments, notches on the proximal surface 610 may be located at asymmetric positions around the longitudinal axis. In other examples, the proximal surface 610 may include more than four notches or less than four notches. Furthermore, in other embodiments, the proximal surface 610 is constructed asymmetrically, shaped conform to the shape of a patient's foot, or with raised portions to compensate for a patient's walking gait characteristics, such as pronation.

Figure 8:
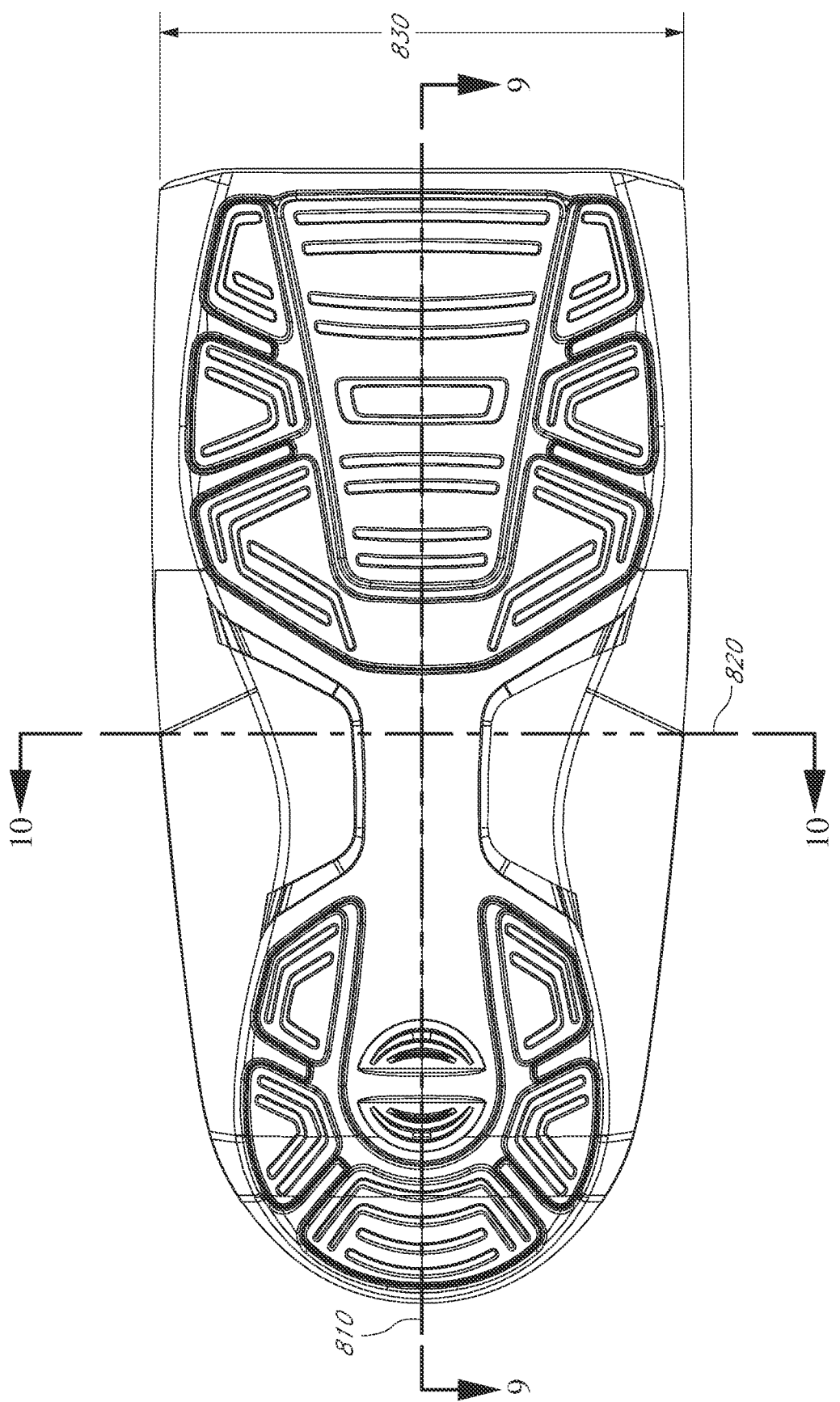
FIG. 8 is a projection of the distal surface of the illustrative curved sole in FIG. 6, in accordance with one embodiment.

FIG. 8 is a projection of the distal surface 620 of the illustrative curved sole 600, according to one embodiment. The anterior-posterior axis 810 divides the sole 600 into two halves, and passes through the posterior point of the sole 600. In some embodiments, the two halves are identical, i.e., the distal surface is symmetric. The distal surface may also be asymmetric. For example, the distal surface 620 may be designed to include arch support, and/or to accommodate pronation of a left or a right foot. The width 830 of the sole 600 is measured across the widest medial-lateral cross-section of the sole 600. In this embodiment, the width 830 is about 45% of the full AP length 625 (see FIG. 6) of the sole 600. When a walking brace is customized according to injury type or user preferences, the ratio between the width 830 of the sole 600 and the full AP length 625 of the sole 600 may be in the range between about 35% to about 55%.

Figure 9:
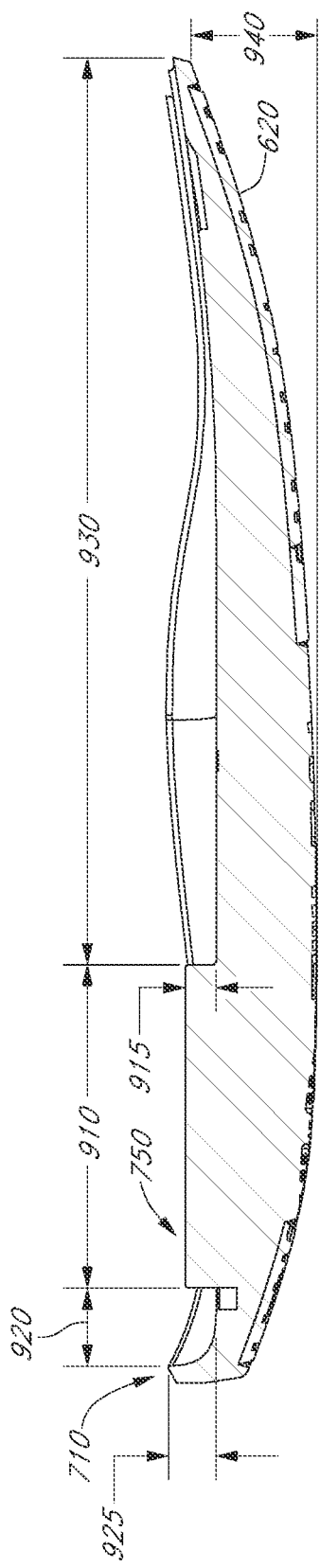
FIG. 9 is an anterior-posterior cross-sectional view of the illustrative curved sole in FIG. 6, in accordance with one embodiment.

FIG. 9 is an anterior-posterior cross-sectional view of the curved sole 600, according to one embodiment. The cross-section is taken at the anterior-posterior axis 810 shown in FIG. 8. The raised platform 750 has a length 910 and a height 915. According to one example, the length 910 is about 2.6 inches and the height 915 is about 0.25 inches. The raised platform 750 is spaced apart from the circumferential rim 710 by a distance 920. In one example, the distance 920 is about 0.5 inches. The rim 710 has a rim height 925 of about 0.4 inches. The rim height 925 of the rim 710 may vary along the edge of the distal surface 620. The thickness 940 of the sole 600 is approximately the same as the distance between the highest point on the distal surface 620 and the ground level. In some embodiments, the thickness 940 of the sole 600 is about 0.75 inches. The thickness 940 of the sole 600 may vary depending on the size of the sole 600.

Figure 10:
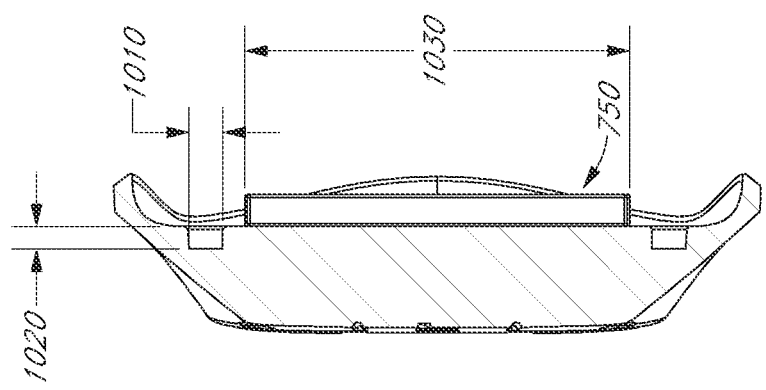
FIG. 10 is a medial-lateral cross-sectional view of the illustrative curved sole in FIG. 6, in accordance with one embodiment.

FIG. 10 is a medial-lateral cross-sectional view of the curved sole 600, wherein the cross-section is made at the medial-lateral line 820 of FIG. 8, perpendicular to the anterior-posterior axis 810. The circumferential groove 720 has a width 1010 and a depth 1020 at the medial-lateral line 820. According to one example, the width 1010 is about 0.25 inches and the depth 1020 is about 0.15 inches. As shown in FIG. 10, the medial-lateral width 1030 of the raised platform 750 is about 3.0 inches at the medial-lateral line 820.

Figure 11:
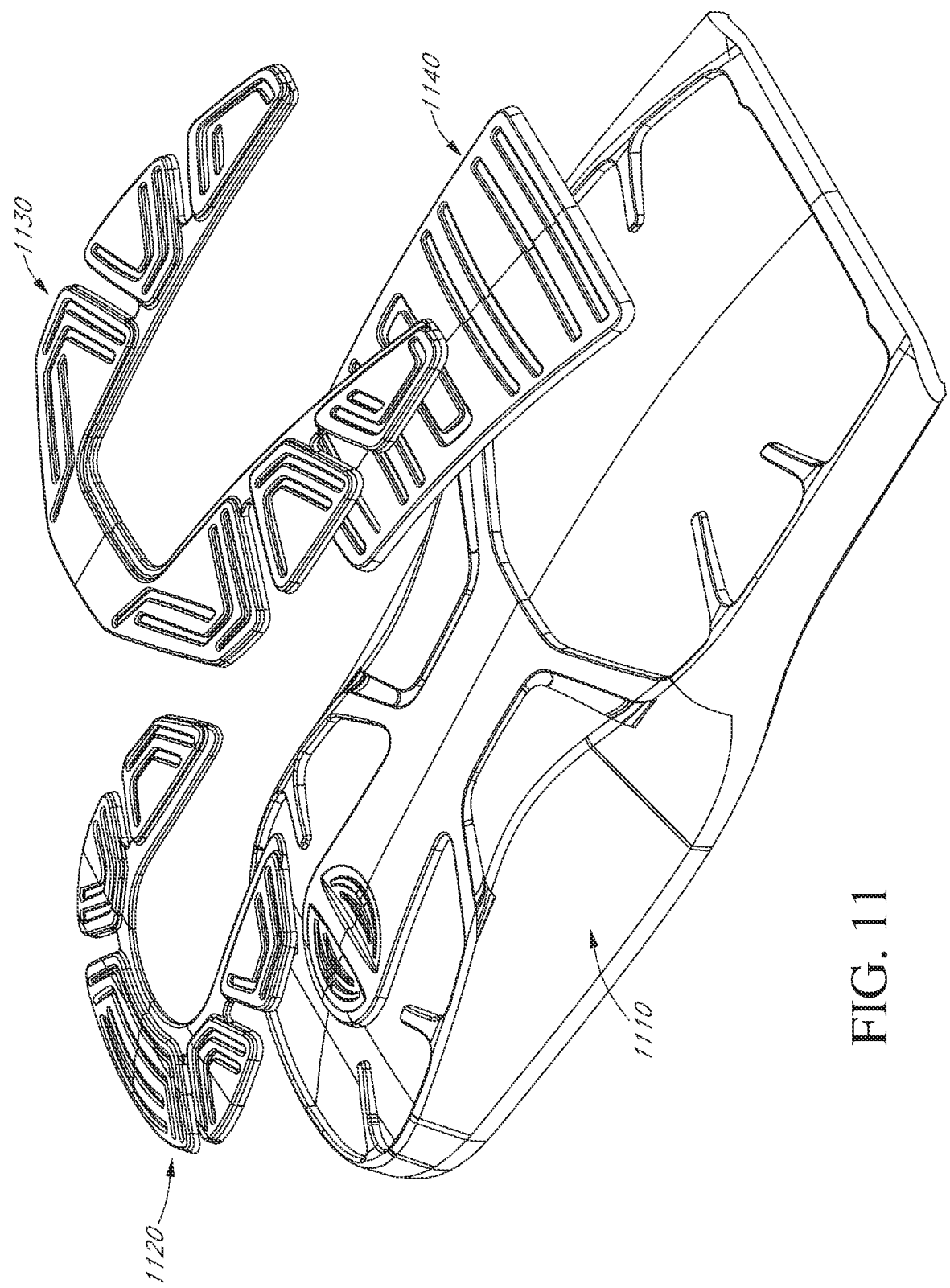
FIG. 11 is an exploded view of the curved sole in FIG. 6, showing an illustrative segmented and layered structure of the distal surface, with segments formed by different materials, in accordance with one embodiment.

FIG. 11 is an exploded view of the distal surface 620 of the curved sole 600 shown in FIG. 6. In practice, the sole 600 can be manufactured using various materials and various processes. In one implementation, the sole 600 is manufactured from a mold using one type of material, for example, vulcanized natural rubber, which is preferred for its anti-slip and shock-absorbing properties. Natural rubber has a high density, and thus adds significant weight to the walking brace. To reduce the overall weight of the sole 600 yet providing shock absorbance and wear resistance, in some implementations, the sole 600 is made by fusing an outsole layer and a midsole layer into a single piece, where the outsole layer corresponds to the distal surface 620 of the sole 600, and the midsole layer corresponds to the proximal surface 610 of the sole 600. The distal surface 620 and the proximal surface 610 can be made of materials with different densities and rigidities.

In some implementations, the distal surface 620 is made of two different types of materials in a segmented and layered structure. As shown in FIG. 11, thin layers of inserts 1120, 1130, and 1140 are made of natural rubber, while the main body 1110 is made of a lighter material such as 100% EVA (Ethyl-Vinyl Acetate), known for its durability and shock-absorbency. The first insert 1120 is placed at around the posterior region of the distal surface 620 to reduce skid during heal-strike, while the second insert 1130 and the third insert 1140 are placed below the anterior region and part of the mid region to minimize slippage during mid-stance and toe-off. The first insert 1120 has a horseshoe shape, which reduces its overall surface area and its weight, without comprising anti-slip and shock-absorbing properties. The second insert 1130 is also shaped like a horse-shoe, with a central hollow portion configured to fit the third insert 1140. The third insert 1140 is shaped like an isosceles trapezoid in this example. All of the three inserts 1120, 1130, and 1140 include patterned grooves. Different shapes for the inserts and different patterns for the grooves can be used in other embodiments. According to various examples, the inserts 1120, 1130 and 1140 may have different colors, possibly matching the colors of other parts of the walking brace. In some configurations, more than, or less than three inserts are included in the distal surface 620. For example, instead of the second insert 1130 and the third insert 1140, a single large insert (not shown) may be placed below the anterior region and part of the mid region of the distal surface 620.

It is to be understood that the foregoing is merely illustrative, and is not to be limited to the details given herein. While several embodiments have been provided by the present disclosure, it should be understood that the disclosed systems and devices and their components may be embodied in any other specific forms without departing from the scope of the disclosure.

Variations and modifications will occur to those of skill in the art after reviewing this disclosure, where disclosed features may be implemented in any combination and sub-combinations (including multiple dependent combinations and subcombinations), with one or more other features described herein. The various features described or illustrated above, including any components thereof, may be combined or integrated in other devices, systems, or methods; moreover, certain features may be omitted or not implemented.

Examples of changes, substitutions and alternations are ascertainable by one skilled in the art and to be made without departing from the scope of the information disclosed herein. All references cited herein are incorporated by reference in their entirety and made part of this application.

What is claimed is:

1. A sole configured for use with an orthopedic walking brace, comprising:
a proximal surface and a distal surface, the proximal surface configured to receive a patient's foot, and the distal surface having a posterior region, a mid region, and an anterior region, wherein:
the posterior region is configured to lie under a heel portion of the patient's foot and has a first anterior-posterior (AP) curvature that increases from a posterior side of the posterior region toward a middle portion of the posterior region and decreases from the middle portion of the posterior region toward the mid region,
the mid region is configured to lie under a center portion of the patient's foot, and
the anterior region is configured to lie under an anterior metatarsal and toe portion of the patient's foot and has a second AP curvature.

2. The sole of claim 1, wherein the distal surface comprises a first material having a first density and a second material having a second density that is smaller than the first density.

3. The sole of claim 2, wherein the first material is rubber.

4. The sole of claim 2, wherein the second material is ethyl vinyl acetate.

5. The sole of claim 1, wherein the anterior region comprises greater than or equal to 30% of an AP length of the distal surface and less than or equal to 40% of the AP length of the distal surface.

6. The sole of claim 1, wherein the mid region comprises greater than or equal to 35% of an AP length of the distal surface and less than or equal to 45% of the AP length of the distal surface.

7. The sole of claim 1, wherein the mid region is configured to lie directly beneath the midfoot.

8. The sole of claim 1, wherein the first AP curvature has a maximum value greater than about 0.25 $inch^{-1}$.

9. The sole of claim 1, wherein a product of an AP length of the posterior region and a maximum value of the first AP curvature has a maximum value less than about 0.7.

10. The sole of claim 1, wherein the second AP curvature has a maximum value greater than about 0.1 $inch^{-1}$.

11. The sole of claim 1, wherein a product of an AP length of the anterior region and a maximum value of the second AP curvature is greater than about 0.35.

12. The sole of claim 1, wherein the mid region is substantially flat.

13. The sole of claim 1, wherein the second AP curvature increases from a posterior side of the anterior region toward a middle portion of the anterior region and decreases from the middle portion of the anterior region toward an anterior side of the anterior region.

14. The sole of claim 1, wherein the distal surface has a first medial-lateral (ML) curvature that has a first peak adjacent to a medial edge, a second peak adjacent to a lateral edge of the distal surface, and is substantially flat in between the first and the second peaks.

15. The sole of claim 1, wherein the distal surface is symmetric.

16. The sole of claim 1, wherein the proximal surface is rigid, and the distal surface is flexible.

17. The sole of claim 1, wherein the proximal surface is formed of a plastic material.

18. The sole of claim 1, wherein a distance between a highest point on the distal surface and a ground surface defines a thickness and a maximum value of the thickness is about 0.75 inches.

* * * * *